United States Patent [19]

Wullschleger et al.

[11] Patent Number: 4,772,375

[45] Date of Patent: Sep. 20, 1988

[54] ANTIFOULING ELECTROCHEMICAL GAS SENSOR

[75] Inventors: Richard E. Wullschleger, Menomonee Falls; Charles S. Applegate, Brookfield, both of Wis.

[73] Assignee: James R. Dartez, New Orleans, La.

[21] Appl. No.: 911,546

[22] Filed: Sep. 25, 1986

[51] Int. Cl.[4] .................................... G01N 27/46
[52] U.S. Cl. .................................. 204/402; 204/1 T; 204/131; 204/147; 204/415; 134/1
[58] Field of Search ............... 204/1 P, 415, 402, 196, 204/147, 130, 131; 134/1

[56] References Cited

U.S. PATENT DOCUMENTS

| | | | |
|---|---|---|---|
| 1,489,743 | 4/1924 | Delius et al. | 204/196 |
| 2,898,282 | 8/1959 | Flook et al. | 204/1 Y |
| 2,913,386 | 11/1959 | Clark | 204/415 |
| 3,098,813 | 7/1963 | Beebe et al. | 204/415 |
| 3,241,512 | 3/1966 | Green | 204/196 |
| 3,275,541 | 9/1966 | Strong | 204/402 |
| 3,314,864 | 4/1967 | Hersch | 204/1 B |
| 3,328,277 | 6/1967 | Solomons et al. | 204/415 |
| 3,496,084 | 2/1970 | Stack | 204/402 |
| 3,526,577 | 9/1970 | Molloy | 204/415 |

Primary Examiner—T. Tung
Attorney, Agent, or Firm—Richard C. Ruppin

[57] ABSTRACT

An antifouling electrochemical gas sensor is disclosed in which the sensor has a cell containing two spaced apart electrodes immersed in an electrolyte and a membrane over an opening in the end of the cell which is immersed in a medium containing varying concentrations of a gas to be sensed, typically oxygen. The electrodes are also connected to an external electrical circuit which indicates the current flow between the electrodes as a result of oxidation and reduction reactions at the electrodes caused by oxygen diffusing through the membrane into the cell. The sensor has a sensing mode during which it functions to indicate the amount of oxygen in the medium. The sensor also has a cleaning mode in which the current flow across the electrodes is in an opposite direction to cause a reaction at one of the electrodes producing a biocidal gas. The biocidal gas diffuses through the membrane from the interior of the cell to the exterior surface of the membrane to kill biological growths and organic deposits on the surface of the membrane and thereby clean the surface of the membrane.

25 Claims, 2 Drawing Sheets

ANTIFOULING ELECTROCHEMICAL GAS SENSOR

This invention relates generally to the sensing of the amount of dissolved gas in a medium and in particular to the self-cleaning of an electrochemical sensor for determining oxygen content of a medium.

An electrochemical cell of the type to which this invention pertains comprises a pair of dissimilar electrodes bridged by an electrolyte and separated from the sample medium by means of a membrane that is permeable to the gas being sensed but impermeable to other constituents of the sample medium and to the electrolyte. The membrane is stretched over a sensing electrode of the cell such as to provide a narrow space for electrolyte between the membrane and the electrode. In the presence of the gas from the sample medium, electrochemical reactions result which produce a potential between the two dissimilar electrodes and cause a current to flow through the electrodes in an external measuring circuit to thereby provide an indication of the amount of oxygen in the sample medium. This type of self-energized electrochemical cell is commonly referred to in the art as a galvanic cell.

A similar type of electrochemical cell to which this invention pertains, known as a polarographic cell, contains the components as in the galvanic cell except that the electrodes are of metals which develop a low potential. Thus, in the polarographic cell, it is necessary to apply an external source of voltage across the electrodes to polarize the electrodes and provide the potential required for cathodic reduction of oxygen. In the galvanic type cell, the reactions at the electrodes are spontaneous due to the higher potential inherently developed between them. Although the polarizing potential in the polarographic cell is required to increase the level of the current flow indicative of oxygen in the sample medium, the magnitude of the current flow is nevertheless a function of the concentration of the oxygen in the medium.

Electrochemical cells which use a semi-permeable membrane to admit oxygen into the cell of the sensor are frequently used in mediums containing a high level of impurities such as in lakes and rivers and sewage disposal systems. Typical impurities that coat and foul the exterior surface of a membrane that is immersed in a sample medium are biological growths such as bacteria, algae and sponges, mineral matter such as calcium and magnesium carbonates, silicates and iron hydroxide, and organic matter such as greases, fats, oils or other polymeric material.

Presently known methods of cleaning the membrane include membrane wipers, electrode grinders and agitators. However, such mechanical devices add complexity, greater expense and new maintenance problems and have not been particularly successful.

SUMMARY OF THE INVENTION

It is the object of this invention to provide a relatively simple electrochemical apparatus and method for cleaning the exterior surface of a permeable membrane covering an end of the apparatus immersed in a sample medium containing biological and/or mineral matter which coats and fouls the membrane surface.

According to the invention, a method and apparatus is provided for cleaning the exterior surface of a gas permeable membrane covering an opening of an electrochemical cell containing an electrolytic liquid. The electrolytic liquid is capable of producing a biocidal gas which is diffused through the membrane to its exterior surface to kill biological growths and dissolve mineral deposits on the exterior surface of the membrane.

An electrochemical sensor includes anode and cathode electrodes immersed in an electrolyte in an electrochemical cell from which a biocidal gas can be generated. An oxygen permeable membrane covers an opening in the cell and separates the interior of the cell and the electrolyte from a medium in contact with the exterior surface of the membrane. During a gas sensing mode of the sensor, oxygen in the medium diffuses through the membrane and causes an electrochemical reaction resulting in ion flow from the cathode to the anode and current flow through an electrical connection from the cathode to the anode. The current causes a voltage which can be measured and is indicative of the oxygen entering the cell and therefore the oxygen content of the medium. If the electrochemical cell is of the polarographic type, the current can be measured and is indicative of the oxygen content of the medium. The biocidal gas is generated by causing a current to flow across the electrodes in a direction opposite to that of the current flow caused by the electrochemical reaction during the sensing mode. The sensor is then in a cleaning mode. The current reversal causes an electrode interchange so that the anode becomes the cathode and the cathode becomes the anode and the reaction at the new anode produces the biocidal gas. The biocidal gas diffuses through the membrane to its exterior surface and kills biological growth and dissolves inorganic mineral deposits on the surface of the membrane. In order to remove the biocidal gas from the electrolyte when the electrochemical sensor is returned to the gas sensing mode, the biocidal gas within the electrolyte may be diffused through activated carbon to cause reduction of the chlorine and its elimination from the electrolyte.

DETAILED DESCRIPTION OF THE EMBODIMENTS OF THE INVENTION

Figure 1:
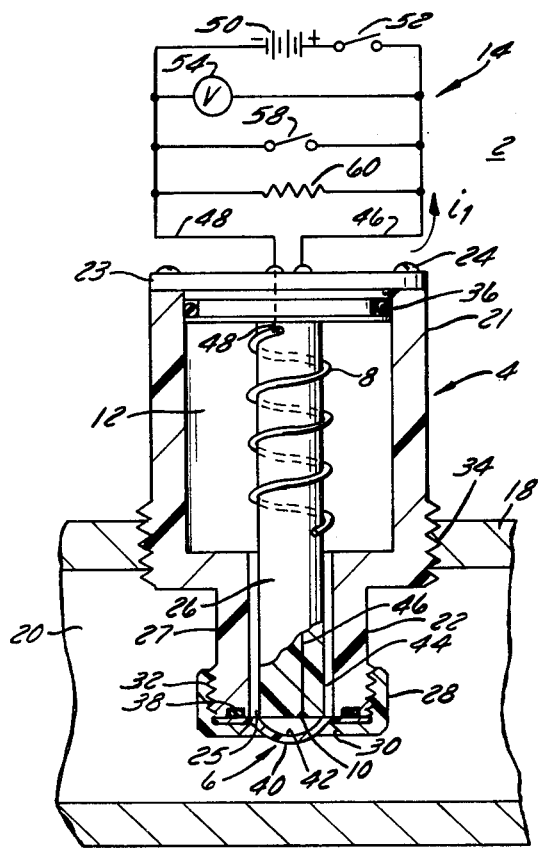
FIG. 1 illustrates the electrochemical sensor according to the invention, partially in cross section, in a sensing mode and extending into a sample medium the oxygen content of which is to be determined.

Referring generally to the Figures of the drawing, an electrochemical sensor 2 is shown as including a cell 4 having an opening 25 at one end 27 covered by a membrane 6, spaced apart electrodes 8 and 10 within the cell 4, an electrolyte 12 in the cell 4 in contact with the electrodes 8 and 10, and an electrical control and sensing circuit 14 connected to the electrodes 8 and 10. The cell 4 is mounted on and extends into a passageway source 18 of a sample medium 20 containing a gas which is to be sensed by the electrochemical sensor.

The cell 4 includes an upper cylindrical wall 21 and a lower cylindrical wall 22, and a first open end which is closed by a cover 23 attached to the container 4 by suitable means such as screws 24. The cover 23 includes a rod 26 extending into the cell 4 and electrolyte 12 in the cell on which are mounted the electrodes 8 and 10. The end 27 is placed in contact with the sample medium 20 and the membrane 6 which covers the opening 25 in the end 27 separates undesired constituents of the sample medium 20 from the interior of the cell 4 and the electrolyte 12 therein. The membrane 6 is held in place on the cell 4 by a cap 28 which is attached to lower cylindrical wall 22 of the cell by suitable means such as threads 32 on the cap 28 and the wall 22. A resilient sealing ring 38 provides a seal between the cap 28 and wall 22. The cell 4 is also mounted on the passageway source 18 by suitable means such as threads 34 in the cell 4 and the passageway 18.

The membrane 6 is preferably of a polymeric material which is permeable to the gas in the sample medium 20 which it is desired to sense and which is at the same time relatively impermeable to undesired ionic species in the sample medium and impermeable to water vapor. The impermeability to water vapor is desirable to minimize the drying up of the electrolyte within the cell 4. For purposes of diffusing dissolved oxygen in the sample medium 20 into the electrolyte 12 within the container 4, a tetrafluoroethylene membrane is preferred.

The sample medium 20 in contact with the membrane 6 may have a high content of inorganic matter and organic biota in the nature of various bacteria and algae. The biological matter will deposit on or cling to the exterior surface 40 of the membrane 6 and prevent dissolved oxygen in the sample medium 20 from reaching and diffusing through the membrane 6. The inorganic matter, consisting primarily of various minerals such as scales of calcium and magnesium carbonates, silicates and iron hydroxide will also coat the membrane 6 and prevent oxygen from diffusing through the membrane into the electrolyte 12. It is also necessary that the biocidal gas generated within the cell 4 be able to diffuse from the interior surface 42 of the membrane 6 through it to its exterior surface 40 to kill the biological deposits and growth and dissolve the mineral deposits on the exterior surface 40. The applicants have found that a tetrafluoroethylene membrane material is also satisfactory for use in diffusing biocidal chlorine gas.

The electrolyte 12 should be of a type which supports a relatively high level of electrical conductivity, is stable, has a relatively constant sensitivity over a wide range of gas concentration, and which, with the electrodes 8 and 10, has a low residual current when the gas constituent being measured is not entering the cell 4. In addition, and quite critically, the electrolyte 12 must be capable of producing a biocidal gas when the sensor is in a cleaning mode which will diffuse through the membrane 6 in adequate amounts to kill biological deposits and growths and dissolve mineral deposits on the exterior surface of the membrane. Suitable electrolytes are those comprising an aqueous solution of a halogen salt. Potassium chloride is preferred for producing the biocidal effect.

With reference to FIG. 1, the electrode 8 is illustrated as a wire wound about the rod 26 and in contact with the electrolyte 12 and the electrode 10 is illustrated as a semispherical piece affixed to the end 44 of the rod 26 and in contact with a thin layer of electrolyte 12 between the electrode 10 and the membrane 6. The electrode 10 is connected by a conductor 46, which extends through the rod 26 and cover 23, to one side of the electrical control and sensing circuit 14. The electrode 8 is connected by a conductor 48, which also extends through the cover 23 to the other side of the circuit 14. During the sensing mode of the electrochemical sensor 2, a reduction reaction takes place at the electrode 10 located adjacent the membrane 6 which is caused by diffusion of gas through the membrane 6 and into the cell 4. An oxidation reaction takes place at the electrode 8 during the sensing mode of the electrochemical sensor. During the gas sensing mode, then, the electrode 10 functions as a cathode and the electrode 8 functions as an anode in the electrical circuit caused by the electrolytic reactions within the cell 4. The electrode 8 and electrode 10 are respectively of materials that are suitable for long-term stable and active oxidation and reduction reactions. It is also desirable that the electrode 10, at which an oxidation reaction will take place during the cleaning mode of the sensor 2 to produce the biocidal gas, be of a material which will not also react to produce a salt at the electrode 10. In the electrochemical sensor 2 of the present invention, a lead anode electrode 8 and a platinum cathode electrode 10 are the preferred materials.

The electrical control and sensing circuit 14 includes a serially connected power source such as battery 50 and switch 52, a volt meter 54, a switch 58, and a resistor 60, all connected in parallel between the conductors 46 and 48.

During the operation of the electrochemical sensor 2, in its sensing mode, where oxygen is the gas in the medium 20 that is being sensed and measured, the oxygen diffuses through the membrane 6. The oxygen causes an electrochemical reduction reaction at the cathode electrode 10. As a result of the reduction reaction, hydroxl ions are freed to migrate to the anode electrode 8. An electrochemical oxidation reaction takes place at the anode electrode 8 and results in electrons being released to cause an electric current $i_1$ to flow from cathode electrode 10 to conductor 46 and through the resistor 60 to the conductor 48 and to the anode electrode 8. Due to the connection of the resistor 60 between the electrodes, a voltage drop is produced by the current $i_1$ flowing through the resistor 60. The voltage drop is measured by the voltmeter 54 to provide an indication which is representative of the amount of oxygen in the medium 20.

Figure 2:
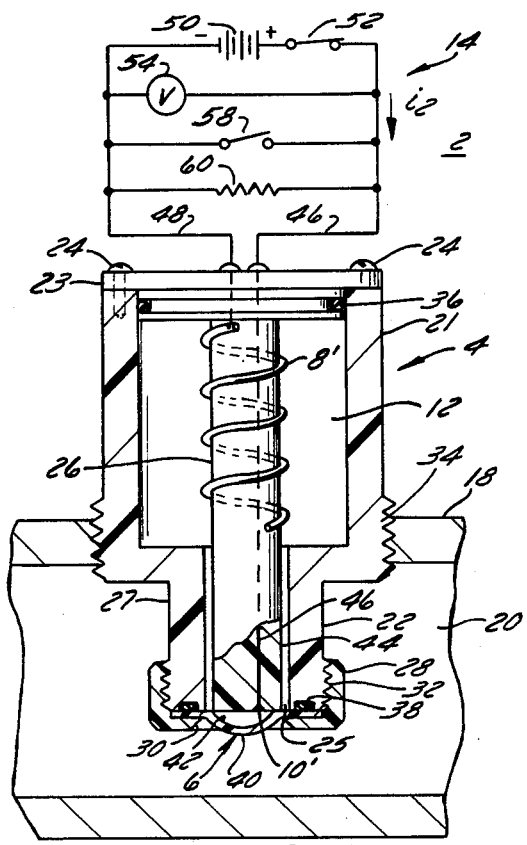
FIG. 2 illustrates the electrochemical sensor shown in FIG. 1 with the sensor in a cleaning mode.

The electrochemical sensor 2 may be placed in a cleaning mode, as shown in FIG. 2, by closing the switch 52 to apply the d.c. voltage of the battery 50 across the conductors 46 and 48 and thereby the electrodes 8 and 10. The battery 50 produces a current $i_2$ in a direction opposite to that of the current $i_1$, within the cell 4 and the portion of the current $i_2$ flowing to the electrodes causes the chloride ions in the electrolyte 12 to be oxidized to chlorine gas. Voltmeter 54 indicates the battery potential applied between the electrodes 8 and 10. Specifically, with reference to FIG. 2, the direction of flow of the current $i_2$ will change or convert the cathode electrode 10 to an anode electrode 10' and the anode electrode 8 to a cathode electrode 8' and correspondingly cause the reduction reaction to take place at the cathode 8' and the oxidation reaction to take place at the anode 10'. The oxidation reaction causes chlorine gas to be generated at the anode 10'. Due to the proximity of the anode 10' to the membrane 6, the chlorine gas will diffuse through the membrane 6 from its interior surface 42 to its exterior surface 40 and kill the biological deposits and growths on the exterior surface 40 of the membrane 6. A chlorine hydrolysis reaction also takes place at the exterior surface 40 of the membrane to produce hypochlorous acid and hydrochloric acids which results in a pH depression at the membrane surface 40 to dissolve the inorganic mineral deposits on the surface. In the cleaning mode of the electrochemical sensor, additional reactions include reduction of the lead oxide on the cathode 8' to thereby regenerate the cathode 8' and also generate some hydrogen gas at the cathode 8'.

Figure 3:
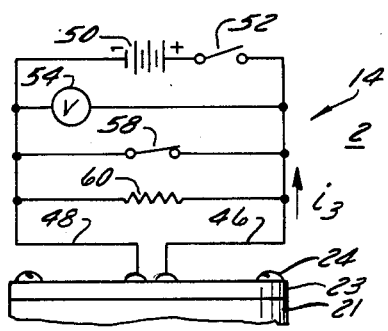
FIG. 3 illustrates the circuit of the electrochemical sensor when the sensor is in a sensing reestablishing mode.

After the exterior surface 40 of the membrane 6 has been saturated with chlorine gas and the maximum possible biota kill and pH depression have been obtained, the sensor 2 is placed in a reestablishment mode as shown in FIG. 3 by opening the switch 52 to disconnect the battery 50 in the circuit 14 and closing the switch 58 to allow a rapid reestablishment of the electrolytic reactions of the cell. The closing of the switch 58 short-circuits the resistor 60 so that the normal electrolytic reactions of the cell will be at a somewhat increased rate and the chlorine gas in the vicinity of the cathode electrode 10 will be reduced more rapidly to eliminate the chlorine from the electrolyte 12. The current flow $i_3$ in the circuit 14 will be high through switch 58 since it provides a lower resistive path than that through resistor 60. After this reconditioning or reestablishing mode, the switch 58 is opened and the switch 56 is closed to reconnect the voltmeter 54 to the circuit 14 and return the electrochemical sensor 2 to its sensing mode.

Figure 5:
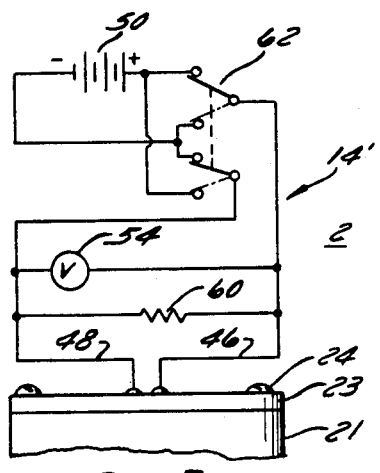
FIG. 5 illustrates another alternate embodiment of the electrochemical sensor.

In an alternate embodiment of the invention in which the circuit 14 is modified to include a double-pole double-throw switch 62, illustrated in FIG. 5, the sensor 2 is placed in the reestablishment mode by keeping the switch 52 closed and moving the switch 62 from its position shown in solid lines to its position shown in phantom lines in FIG. 5 for a short time. This reverses the connection of the positive and negative terminals of the battery 50 and thereby reverses the current in circuit 14 to accelerate reduction of chlorine at cathode electrode 10 and depolarization of the electrodes. Following the reestablishing mode using the switch 62, the switch 52 is opened and the switch 62 returned to its position shown in solid lines in FIG. 5.

Figure 4:
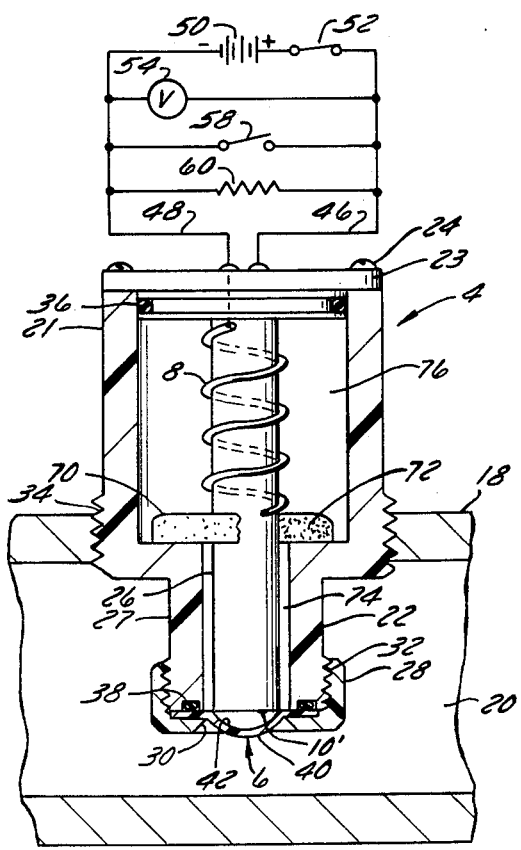
FIG. 4 illustrates an alternate embodiment of the electrochemical sensor.

An alternate embodiment of the invention is illustrated in FIG. 4 in which a porous container 70 of activated carbon material 72 is positioned between a narrowed chamber area 74 and a larger area chamber 76 of the cell 4. The narrowed area 74 is adjacent the location of the generation of the chlorine gas at the anode 10' and in the path of chlorine gas generated during the cleaning mode of the sensor 2 that remains in the cell 4 and may move from the narrow chamber 74 to the wide chamber 76. The chlorine gas diffuses into and contacts the activated carbon 70 and reacts with the carbon and water to form hydrochloric acid and carbon dioxide. Where the chlorine gas has formed hypochlorous acid in the cell 4, dechlorination in which the activated carbon 70 acts as a catalyst also takes place and the reaction products are hydrochloric acid and carbon dioxide. Through these two reactions, the residual chlorine gas is substantially destroyed. Although the use of the switch 58 to short-circuit the resistor 60 increases the rate of the chlorine reduction reaction, as previously described with respect to the reestablishment mode of the sensor 2, the time to return the electrochemical sensor to the sensing mode is nevertheless excessively long, since chlorine that diffuses into the electrolyte is retained within the cell 4 for a considerable time and results in erroneous readings during that time. The addition of the activated carbon 72 greatly accelerates the chlorine destruction rate to minimize the time required to return the sensor 2 to its sensing condition.

Figure 6:
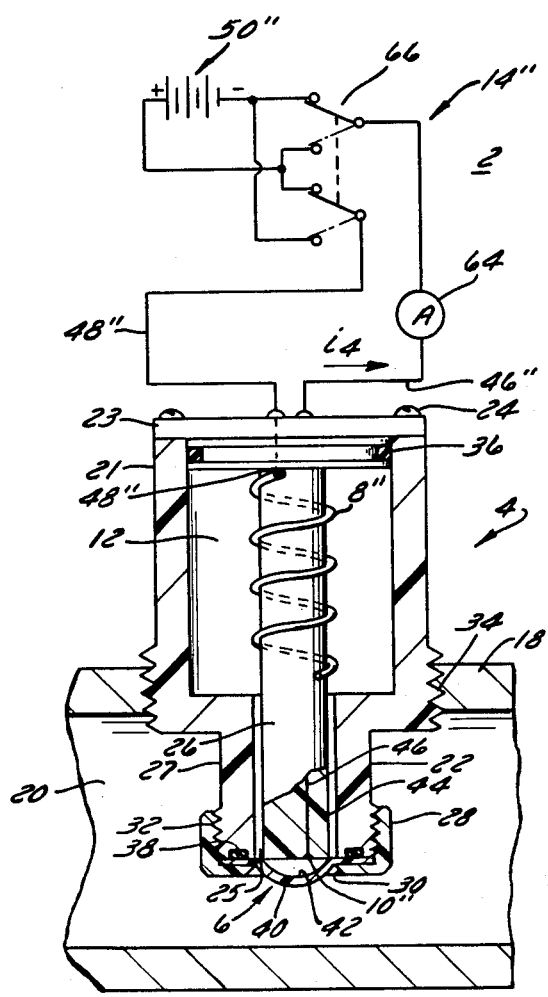
FIG. 6 illustrates a further alternate embodiment of the electrochemical sensor.

Another alternate embodiment of the invention is shown in FIG. 6 in which the electrochemical sensor 2 is of a polarographic sensor. Thus the anode electrode 8" and the cathode electrode 10" are of metals which develop a low electrochemical potential between them such as a gold cathode and a silver anode. The circuit 14" in the polarographic sensor illustrated in FIG. 6 also differs from the circuit 14 illustrated in the embodiments of the invention illustrated in FIGS. 1-5 in that the battery 50" is connected across the electrodes during the oxygen sensing mode of the sensor 2 with a polarity that causes polarization of the electrodes. When oxygen diffuses through the membrane 6, the electrochemical reactions will take place as described with reference to the embodiments of the electrochemical sensor shown in FIGS. 1-4 and a current $i_4$ will flow from the cathode 10" through the conductor 46", the ammeter 64 and the conductor 48" to the anode 8". The current measured by the ammeter 64 will provide an indication which is representative of the amount of oxygen in the medium 20. In order to place the sensor 2 in the cleaning mode, the switch 66 is moved from its solid line position to its phantom line position as shown in FIG. 6. This reverses the potential of the battery 50" across the electrodes and, as in the embodiments illustrated in FIGS. 1-4, causes the generation of a biocidal gas from the electrolyte 12 in the cell 4 which diffuses through the membrane 6 to its exterior surface 40 and kills biological deposits on the exterior surface 40 of the membrane 6 and dissolves inorganic mineral deposits on the surface 40. The sensor 2 shown in FIG. 6 is returned to its sensing mode by moving the switch 66 from its phantom line position to the full line position as shown in FIG. 6.

Although several embodiments of the invention have been disclosed herein for purposes of illustration, it will be understood that various changes can be made in the form, details, arrangement, proportions and materials of the various parts in such embodiments without departing from the spirit and scope of the invention as defined by the appended claims.

What is claimed is:

1. A method of cleaning the exterior surface of a gas permeable membrane covering an opening of an electrochemical cell having a pair of spaced apart electrodes comprising the steps of:
   placing an electrolytic liquid in the cell in contact with the electrodes and with an interior surface of the membrane;
   applying a d.c. voltage across the electrodes to cause an electrochemical reaction generating a biocidal gas from the electrolytic liquid; and
   diffusing the gas through the membrane to its exterior surface to kill biological deposits on the exterior surface of the membrane.

2. The method according to claim 1 wherein the electrolytic liquid is an aqueous solution of a halogen salt.

3. The method according to claim 1 wherein the biocidal gas dissolves mineral deposits on the exterior surface of the membrane.

4. The method according to claim 1 wherein the biocidal gas is chlorine; and further comprising the step of reacting the chlorine with water at the exterior surface of the membrane to produce hypochlorous and hydrochloric acid for dissolving mineral deposits on the membrane.

5. The method according to claims 1, 2, 3 or 4 further comprising the step of generating a reaction with the biocidal gas remaining in the cell to cause the destruction of the biocidal gas.

6. The method according to claims 1, 2, 3 or 4 further comprising the steps of:

contacting biocidal gas remaining in the cell with a reactive material; and destroying the biocidal gas by a reaction with said material.

7. A method of measuring oxygen gas in a sample medium with an electrochemical sensor having a cell containing a pair of spaced apart electrically connected anode and cathode electrodes, an oxygen permeable membrane covering an opening in the cell and separating the electrodes from the sample medium, the membrane having an exterior side in contact with the sample and an interior side facing the interior of the cell, comprising the steps of:

placing an electrolyte from which a biocidal gas can be generated in the cell in contact with the anode and cathode and the interior surface of the membrane;

diffusing oxygen in the sample medium through the membrane;

reducing the oxygen at the cathode to produce an electrolytic current to the anode;

oxidizing the anode to produce a first current flowing from the cathode to the anode through the electrical connection between the anode and cathode and sensing the first current as a measure of oxygen gas in the sample medium;

applying a d.c. voltage across the anode and cathode electrodes inducing a second current flowing in a direction opposite to that of the first current due to the electrochemical reactions to cause a reaction generating from the electrolyte a biocidal gas at the converted anode; and diffusing the biocidal gas through the membrane to the exterior surface of the membrane to kill biological deposits on the exterior surface.

8. The method according to claim 7 wherein the electrolyte is an aqueous solution of a halogen salt.

9. The method according to claim 7 wherein:

the first current flowing from the cathode to the anode flows through a resistor to provide a voltage drop indicative of the oxygen content of the sample medium; and further comprising removing the d.c. voltage and short-circuiting the resistor following the killing of the biological deposits on the membrane to reestablish the reduction and oxidation reactions producing said first current; and removing the short-circuit of the resistor to cause the first current flowing from the cathode to the anode to again flow through the resistor.

10. The method according to claims 7 or 8 further comprising the steps, following the diffusing of the biocidal gas through the membrane, of generating a reaction with the biocidal gas remaining in the cell to cause its destruction.

11. The method according to claim 7, 8 or 9 further comprising the steps of:

contacting biocidal gas remaining in the cell with a reactive agent; and destroying the biocidal gas by a reaction with the agent.

12. The method according to claim 11 wherein the reactive agent is activated carbon.

13. The method according to claim 12 wherein the reaction is a catalytic reaction.

14. The method according to claim 10 wherein the biocidal gas destruction step is accomplished by reversing the polarity of the d.c. voltage to increase the level of the first current and reduce the biocidal gas at the cathode electrode.

15. An electrochemical sensor for sensing oxygen in a sample medium and having a cell containing a pair of spaced apart electrically connected anode and cathode electrodes, an oxygen permeable membrane covering an opening in the cell and separating the electrodes from the sample medium, oxygen entering the cell through the membrane from the sample medium, and an interior surface facing the interior of the cell and an exterior surface in contact with the sample medium, comprising:

an electrolyte within the cell in contact with both electrodes and the interior surface of the membrane, the electrolyte being such as to provide a first polarity and conductivity for ions between the electrodes in accord with said first polarity as a result of reactions due to oxygen entering the cell through the membrane;

energy means connectable between the electrodes in a manner such that the electrodes have a second polarity opposite to that of the first polarity;

a biocidal gas within the cell, said gas being produced in a reaction at one of the electrodes in response to the connection of the energy means to the electrodes; and the membrane being also permeable to the biocidal gas whereby the gas diffuses through the membrane such that the biocidal gas is in contact with the exterior surface and kills biological deposits on the exterior surface.

16. The electrochemical sensor according to claim 15 wherein the electrode at which the biocidal gas is produced is of a material that will not react with the gas to produce a salt.

17. The electrochemical sensor according to claim 15 further comprising reactive means separate from the electrodes and contacting biocidal gas remaining in the cell after the biological deposits have been killed for generating a reaction destructive of the biocidal gas.

18. The electrochemical sensor according to claim 17 wherein the reactive means comprises activated carbon.

19. The electrochemical sensor according to claim 15 further comprising means for reversing the polarity of the energy means from said second polarity for causing a reduction reaction of the biocidal gas at the cathode electrode which remains in the cell after the killing of the biological deposits.

20. A method of sensing oxygen gas in a sample medium with an electrochemical sensor including a cell having an oxygen permeable membrane covered end immersed in the sample medium and removing biological matter deposited on an exterior surface of the membrane from the sample medium, the cell containing a pair of spaced apart electrically connected anode and cathode electrodes and an electrolyte in contact with the electrodes and an interior surface of the membrane, comprising the steps of:

in a sensing mode of the electrochemical sensor, diffusing oxygen from the sample medium through the membrane and producing electrochemical reactions within the cell at the electrodes causing a first current flow between the electrodes indicative of the oxygen content of the sample medium;

in a cleaning mode of the electrochemical sensor, stopping said electrochemical reactions, producing a second current flow between the electrodes opposite to the direction of the flow of the first current to thereby generate a biocidal gas from the electrolyte at one of the electrodes, and diffusing the biocidal gas through the membrane to its exterior surface to kill and thereby remove biological matter on the membrane; and in a reestablishment mode of the electrochemical sensor, terminating the flow of the second current between the electrodes and thereby stopping the generation of the biocidal gas, generating reactions destructive of the biocidal gas remaining in the cell, and returning the electrochemical sensor to its sensing mode.

21. The method according to claim 20 wherein the biocidal gas destructive reactions are accomplished by contacting the biocidal gas with a reactive material causing a reductive reaction with the biocidal gas.

22. The method according to claim 21 wherein the reactive material is activated carbon.

23. The method according to claims 20, 21 or 22 wherein the electrolyte comprises an aqueous solution of a halogen salt.

24. A method of measuring oxygen gas in a sample medium with an electrochemical sensor having a cell containing a pair of spaced apart electrically connected anode and cathode electrodes, an oxygen permeable membrane covering an opening in the cell and separating the electrodes from the sample medium, the membrane having an exterior side in contact with the sample and an interior side facing the interior of the cell, comprising the steps of:

placing an electrolyte from which a biocidal gas can be generated in the cell in contact with the anode and cathode and the interior surface of the membrane;

applying a first d.c. voltage across the anode and cathode electrodes with the negative polarity applied to the cathode electrode so that sufficient potential is available at the cathode for the reduction of oxygen;

diffusing oxygen in the sample medium through the membrane;

reducing the oxygen at the cathode to produce an electrolytic current to the anode;

oxidizing the anode to produce current flow from the cathode to the anode through the electrical connection between the anode and cathode and sensing the current flow as a measure of oxygen gas in the sample medium;

applying a second d.c. voltage across the anode and cathode electrodes having a polarity opposite to that of the first d.c. voltage and inducing a current flow opposite to that of the current flow due to the electrochemical reactions to cause a reaction generating from the electrolyte a biocidal gas at the converted anode; and diffusing the biocidal gas through the membrane to the exterior surface of the membrane to kill biological deposits on the exterior surface.

25. The method according to claim 24 wherein the electrolyte is an aqueous solution of a halogen salt.

* * * * *